United States Patent [19]

Stracher et al.

[11] Patent Number: 4,742,081

[45] Date of Patent: May 3, 1988

[54] CARNITINE COUPLED PHARMACEUTICAL AGENTS

[76] Inventors: Alfred Stracher, 47 The Oaks, Roslyn Estates, N.Y. 11576; Leo Kesner, 1726 E. 32 St., Brooklyn, N.Y. 11234

[21] Appl. No.: 816,546

[22] Filed: Jan. 6, 1986

[51] Int. Cl.$^4$ ............................................ A61K 31/225
[52] U.S. Cl. .................................................. 514/547
[58] Field of Search ....................................... 514/547

[56] References Cited

U.S. PATENT DOCUMENTS 4,401,827 8/1983 Witt ........................................ 560/55

Primary Examiner—Stanley J. Friedman
Attorney, Agent, or Firm—Sprung Horn Kramer & Woods

[57] ABSTRACT

Carnitine, which preferentially accumulates in cardiac and skeletal muscle, is coupled to a protease inhibitor, or any other pharmaceutically active compound for the purpose of site-specific drug delivery to these tissues.

These products may be useful in a variety of muscle wasting diseases. They may also be useful in a variety of cardiac conditions including those produced by cardiac ischemia. They may also be useful as growth promoters for animals.

6 Claims, No Drawings

CARNITINE COUPLED PHARMACEUTICAL AGENTS

The present invention relates to the provision of novel pharmaceutically active compounds which will preferentially be delivered to preselected sites in the patient's body, and to intermediates therefor.

It is known that certain compounds when administered to patients preferentially concentrate in selected tissues.

It is also known that carnitine, a compound of the formula

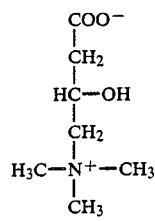

and commercially available in large quantity is readily concentrated by active transport in cardiac and skeletal muscle at 50-100 times the concentration found in plasma. The physiological function of carnitine is to transport long and short chain fatty acids into cells and across mitochondrial membranes bound through an ester linkage.

Finally it is known that certain compounds are protease inhibitors. Leupeptin is one such material, as described in U.S. Pat. No. 4,510,130, issued Apr. 9, 1985.

It is accordingly an object of the invention to utilize these concepts and provide pharmaceuticals which, though not per se selectively deliverable, can be rendered selectively deliverable to predetermined tissues.

It is a further object of the invention to provide pharmaceuticals which are preferentially deliverable to cardiac and skeletal muscle.

These and other objects and advantages are realized in accordance with the present invention pursuant to which compounds which upon administration preferentially concentrate in certain tissues, and are utilized to carry pharmaceutically active compounds to such sites. This carrier action is accomplished by providing a chemical linkage which does not interfere with either the carrier action or pharmaceutical activity.

In accordance with one aspect of the invention, the carrier is a compound which preferentially travels to cardiac and skeletal muscle, e.g., carnitine of the formula

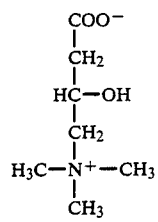

Advantageously this is linked through the hydroxyl group, preferably as an ester, to a pharmaceutically active material, e.g., leucyl argininal of the formula

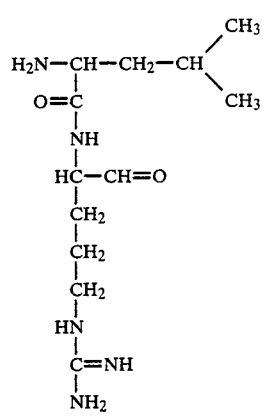

The linkage is preferably through the amino group which is connected to a —CH— radical, by means of a bifunctional radical. Thus, the carnitine and leucyl argininal can be linked by a polyfunctional reagent, the carnitine can be esterified with an acid carrying a functional group and then this functional group and the NH₂ of leucyl argininal can be linked, or the leucyl argininal can be reacted with a reagent carrying a second functional group and this can be linked to the carnitine in the next step. If desired or necessary, other reactive sites may be temporarily blocked.

In this approach, advantageously the carnitine is first esterified, preferably with an aminoalkanecarboxylic acid or perhaps an alkanedicarboxylic acid, leaving an amine or carboxyl group hanging free. Then this is joined to the pharmaceutical by a bifunctional reagent such as a dialdehyde, e.g., glutaraldehyde, a carbodiimide, a diisocyanate, and the like. In other words, the linkage between the two ends of the new molecule may be in one step, or in two or more steps. The connector can be aliphatic or aromatic and can be substituted in the chain or on the side. Substitutions in the chain can result from the use of particular linking agents such as those carrying amino, carboxyl, carbonyl, alcohol and/or thiol groups, amino and carboxyl being preferred.

In accordance with another aspect of the invention, the protease inhibitor linked to the carnitine can be pepstatin, of the formula

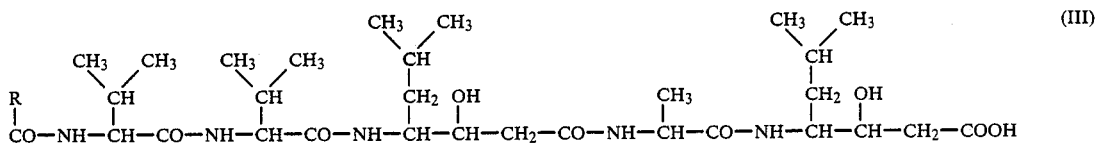

where R may be:

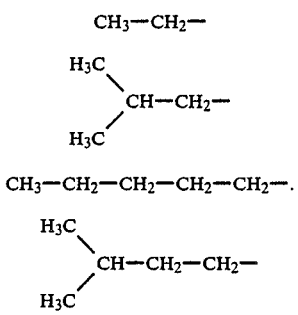

Advantageously aside from connecting functional groups as described above, the linkages involve lower aliphatic radicals, i.e., containing up to about 22 atoms. A suitable first reagent is ε-aminocaproic acid, which is readily available commercially. Ester formation with carnitine (I), for example, will proceed by reacting with the acid chloride of ε-aminocaproic acid (IV). The ester is then joined to leucylargininal dibutylacetal by glutaraldehyde.

Carnitine (I) ε-Aminocaproic acid chloride (IV)

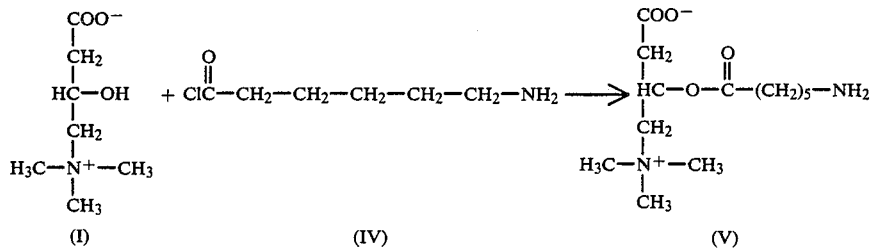

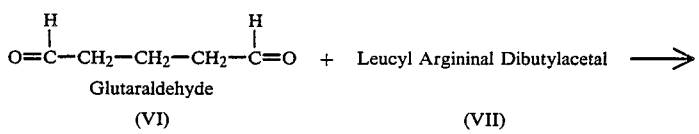

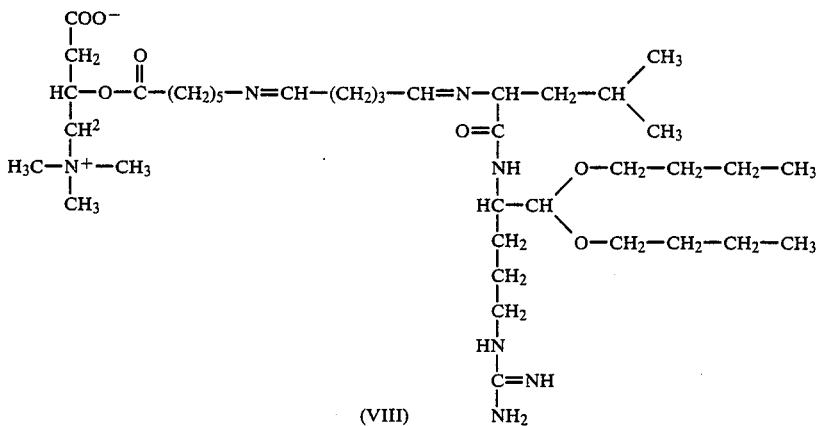

In a similar vein carbodiimide can be used in place of glutaraldehyde as the linking agent using glutaric acid as a connector. Thus the carnitine can be linked to the leucyl argininal by an alkylene-X-alkylene linkage, wherein X is —N—, —NH—, —NH—NH—, —O—, —S—, —CONH—, or the like, the two ends being sufficiently spaced so as not to interfere with one another biologically.

The leucyl argininal starting material is prepared from leupeptin.

It is not known if the activity is because the carnitine or other carrier permits the leucyl argininal to be present at a site in high concentration whereas the unlinked leucyl argininal itself cannot reach a therapeutic level.

Other protease inhibitors or precursors thereof, such as leupeptin, pepstatin, or the like, can also be employed.

It is not known if the materials act by hydrolysis to release the linked pharmaceutical after it has been delivered to the desired site or if the pharmaceutical functions in a linked state because its active groups are free to perform.

Because of the selective concentration at a particular site, it is possible to achieve at such sites a concentration of pharmaceutical which heretofore could have been achieved only by using a much higher overall dosage, perhaps such a high dosage as would be toxic or dangerous.

The linked materials are soluble in water or isotonic solution and can be administered to animals, human and otherwise, as well as to plants in any conventional manner, i.e., as solutions, tablets or capsules, depending upon the desired manner of administration, e.g., per os, injection, etc.

The carnitine is physiologically acceptable so the limiting factor on dosage is the pharmaceutical which, as already noted, can be a pharmaceutical precursor. Thus, for example, in administering carnityl leucyl argininal to chickens in accordance with the invention to enhance their growth by protease inhibition, about 1 mg/kg of body weight per day of linked compound VIII is useful, administered in the drinking water or admixed in the feed.

In general the dosage for animals may range from about 0.1 to 10 mg/kg/day in one dose or spread over several doses.

Fillers such as starch, cellulose, lactose, etc., may be admixed to facilitate dosage, and/or other active materials can be included.

The invention will be further described in the following illustrative examples wherein all parts are by weight unless otherwise expressed.

EXAMPLE 1

Preparation of Leucylarginal Dibutyl Acetal

Leupeptin (a mixture of N-acetyl and N-propionyl leucylleucylarginal) is converted to the chloride salt by passing it through a Dowex 1×8 (Cl$^-$) column. The material is eluted with water and fractions are collected. Each fraction is tested for leupeptin by thin layer chromatography on silica gel using the upper phase of the solvent mixture butanol-acetic acid water (4:1:5). Visualization is with iodine vapor. The fractions containing the leupeptin are combined and are evaporated to dryness on a Rotovap at room temperature.

The dry residue is taken up in butanol and refluxed for 2 hours. This produces the dibutyl acetals of leupeptin.

$$Ac-N(H)-leu-C(=O)-N(H)-leu-Arg\begin{matrix}O\,But\\O\,But\end{matrix}$$

An equal volume of butanol and double the volume of water are added in a separatory funnel. After extraction, the upper phase is removed and dried overnight with sodium sulfate. The solvent is then removed with a Rotovap.

To purify the acetals, they are separated on a silica gel column using a gradient starting with chloroform and ending with 60% butanol/chloroform. The purified N-propionyl and N-acetyl forms are identified by thin layer chromatography as described above. The fractions are pooled and evaporated to dryness.

Cleavage of the N-propionyl and N-acetyl leucine is accomplished by reaction with the enzyme thermolysin. This is done at pH 8, over a 72 hour incubation period. The reaction is followed by measuring the release of free amino groups by the TNBS reaction.

$$Ac-N(H)-leuCOO^- + H_2N\,leuArg\begin{matrix}O\,But\\O\,But\end{matrix}\quad(VII)$$

The leucylarginal dibutyl acetal is isolated from this mixture by chromatography on a silica gel column as previously described. The fractions are identified by thin layer chromatography and the solvent is removed. The dry residue is stored in the freezer.

EXAMPLE 2

Preparation of Carnityl-ε-Amino Caproate Ester

The acid chloride of ε-aminocaproic acid is formed by reaction with oxalyl chloride at 0° C.

$$H_2N-(CH_2)_5-COOH + (COCl)_2 \longrightarrow H_2N(CH_2)_5-\underset{O}{\overset{\|}{C}}-Cl$$

(II)        (IV)

Excess oxaylyl chloride is evaporated off and the acid chloride is then dissolved in acetonitrile. Solid carnitine is then added and the ester (V) is formed. The solvent is removed by evaporation.

EXAMPLE 3

Coupling by the Carbodiimide Method

One way for coupling the leucylarginal to the ester is through the carbodiimide reaction.

Glutaric acid (1 mMol) is reacted with 2 equivalents of 1-ethyl-3-(3-dimethyl aminopropyl) carbodiimide (CDI)

$$CH_3-CH_2-N=C=N-CH_2-CH_2-CH_2-N\begin{matrix}CH_3\\CH_3\end{matrix}$$

in 2 ml H$_2$O at room temperature for 30 minutes to produce $$\begin{matrix}R_1NH&O&&O&N-R_1\\|&\|&&\|&|\\HC-&C-(CH_2)_3-C-&CH\\|&&&|\\R_2N&&&NR_2\\H&&&H\end{matrix}$$

To this is added 1 equivalent of leucylarginal dibutylacetal.

$$\begin{matrix}H\\R^1N&O&&O&&&O\,But\\|&\|&&\|&&&/\\HC-C-(CH_2)_3-C-N-leu\,Arg\\|&&&&H&&\backslash\\N&&&&&&O\,But\\R_2-H\end{matrix}$$

This is followed by 1 equivalent of carnityl-ε-aminocaproate $$Carn-cap-\underset{H}{N}-\underset{\|}{\overset{O}{C}}-(CH_2)_3-\underset{\|}{\overset{O}{C}}-\underset{H}{N}-leu\,Arg\begin{matrix}O\,But\\O\,But\end{matrix}$$

The substance is partially purified by chromatography on a Sephadex G10 column. Elution is with water and fractions are tested for trypsin inhibition activity before and after hydrolysis at pH 2, 60° C. for 3 hours. The fractions with activity are neutralized, evaporated to dryness and checked for purity by thin layer chromatography.

It will be understood that the specification and examples are illustrative but not limitative of the present invention and that other embodiments within the spirit and scope of the invention will suggest themselves to those skilled in the art.

What is claimed is:

1. A method of treating cardiac and skeletal muscle in a patient in need thereof which comprises administering to said patient an amount of a pharmaceutical effective therefor which pharmaceutical is chemically linked to

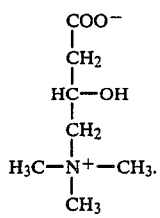

2. The method according to claim 1, in which the linked pharmaceutical is of the formula

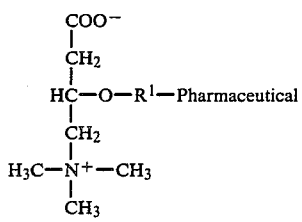

and R¹ is a linking organic radical.

3. The method according to claim 2, in which R¹ is alkylene-X-alkylene, and

X is —N=, —NH—, —NH—NH, —O—, —S— or —CONH—.

4. The method according to claim 2, in which the pharmaceutical is

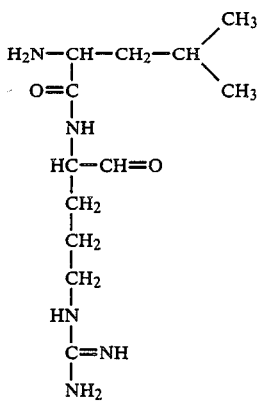

or an acetal thereof.

5. The method according to claim 3, in which alkylene is n-pentylene.

6. The method according to claim 5, in which the linked pharmaceutical is of the formula

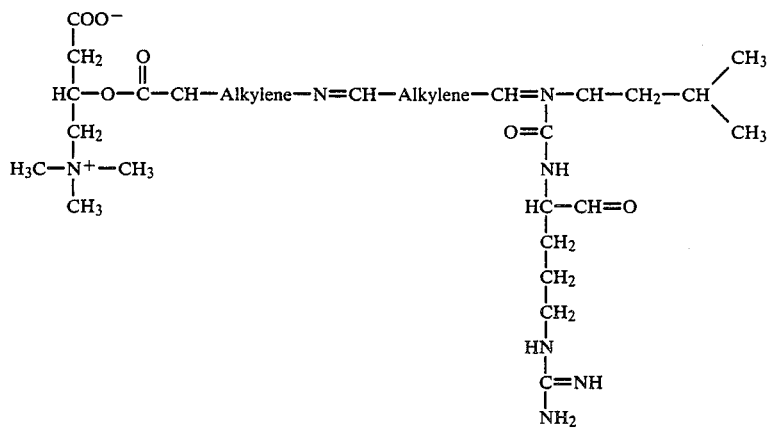

or an acetal thereof.

* * * * *